(12) United States Patent
Deeley et al.

(10) Patent No.: US 6,309,893 B1
(45) Date of Patent: *Oct. 30, 2001

(54) ASSAY METHOD WITH IMPROVED RELEASE OF SOLUBLE REAGENTS

(75) Inventors: George Deeley, High Wycombe; Janys Elizabeth Fletcher, Bagshot, both of (GB)

(73) Assignee: Applied Research Systems ARS Holding NV (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/809,394
(22) PCT Filed: Sep. 20, 1995
(86) PCT No.: PCT/GB95/02236
§ 371 Date: May 16, 1997
§ 102(e) Date: May 16, 1997
(87) PCT Pub. No.: WO96/09549
PCT Pub. Date: Mar. 28, 1996

(30) Foreign Application Priority Data

Sep. 20, 1995 (GB) .................................................... 9419001

(51) Int. Cl.⁷ .................................................. G01N 33/543
(52) U.S. Cl. ........................ 436/518; 436/528; 435/7.32; 435/6

(58) Field of Search ...................... 435/6, 7.32; 436/518, 436/528

(56) References Cited

U.S. PATENT DOCUMENTS 3,993,073 * 11/1976 Zaffaroni .............................. 424/424

(List continued on next page.)

FOREIGN PATENT DOCUMENTS

| 0171148 | 2/1986 | (EP) . |
| 0422708 | 4/1991 | (EP) . |
| 90/05303 | 5/1990 | (WO) . |
| 90 11830 | 10/1990 | (WO) . |
| 90 14590 | 11/1990 | (WO) . |
| 9209892 * | 6/1992 | (WO) . |
| 93 25892 | 12/1993 | (WO) . |
| 93 25908 | 12/1993 | (WO) . |
| 93/25908 | 12/1993 | (WO) . |

OTHER PUBLICATIONS

Lechuga, L. M. et al, 1995, Rev. Plast. Mod., vol. 70 No. 470, Aug., pp. 132–140.*

(List continued on next page.)

*Primary Examiner*—Lynette R. F. Smith
*Assistant Examiner*—Ginny Allen Portner
(74) *Attorney, Agent, or Firm*—Ostrolenk, Faber, Gerb & Soffen, LLP

(57) ABSTRACT

An improved assay method and device for use in such method in which soluble releasable reagents are used.

13 Claims, 1 Drawing Sheet

U.S. PATENT DOCUMENTS

| | | | | |
|---|---|---|---|---|
| 4,203,441 | * | 5/1980 | Theeuwes | 604/892.1 |
| 4,220,152 | * | 9/1980 | Dresback | 424/439 |
| 4,267,280 | * | 5/1981 | McCormick | 525/56 |
| 4,478,818 | * | 10/1984 | Shell et al. | 424/426 |
| 4,657,582 | * | 4/1987 | Huber | 71/121 |
| 4,708,765 | | 11/1987 | Newman et al. | 156/626 |
| 4,990,335 | * | 2/1991 | Bateman et al. | 424/408 |
| 5,015,843 | * | 5/1991 | Seitz et al. | 250/227.21 |
| 5,252,494 | * | 10/1993 | Walt | 436/528 |
| 5,324,649 | * | 6/1994 | Arnold | 435/187 |
| 5,485,277 | * | 1/1996 | Foster | 356/445 |
| 5,506,148 | * | 4/1996 | Munkholm | 436/111 |
| 5,533,393 | * | 7/1996 | Boone | 73/355.02 |
| 5,556,743 | * | 9/1996 | Gibboni | 435/4 |
| 5,582,170 | * | 12/1996 | Soller | 128/634 |
| 5,591,454 | * | 1/1997 | Kuczynski et al. | 424/486 |
| 5,631,170 | * | 5/1997 | Attridge | 436/518 |
| 5,639,468 | * | 6/1997 | Rodgers et al. | 424/426 |
| 5,643,721 | * | 7/1997 | Spring et al. | 435/6 |
| 5,648,213 | * | 7/1997 | Reddy | 435/6 |
| 5,713,852 | * | 2/1998 | Anthony et al. | 604/49 |
| 5,726,064 | * | 3/1998 | Robinson | 436/514 |
| 5,863,558 | * | 1/1999 | Jao et al. | 424/465 |

OTHER PUBLICATIONS

Brook, I.M. et al, Biomaterials, 1986, vol. 7, #4, pp. 292–296.*

Battinelli, L et al, J. Chromatog, 1996, Nov. 6, vol. 753 #1, pp. 47–55.*

Mirth, DB et al, J. Dent. Res., vol. 68(8), 1989, pp. 1285–1288.*

Iwata, H. et al, J. of Membrane Sci, 1991, vol. 55, #1–2, pp. 119–130.*

Langer, R, Methods Enzymol., vol. 73, pp. 57–73, 1981.*

Langer, R et al, Nature, vol. 263, pp. 797–799, 1976.*

Nakagawa, T et al, 1990, vol. 33, pp. 669–670, Rep. on Prog. in Polymer Phys. in Japan.*

Watano, S. et al, Chem. Pharm. Bull., vol. 41, #3, 1993, pp. 580–585.*

Langer, R., Science, vol. 249, pp. 1527–1533, 1990, Sep. 28.*

Watts, P.J. et al, J. of Controlled Release, vol. 16 (1991) pp. 311–318.*

Greenwald, R.B et al, J. Bioactive & Compatible Polymers, 1992, vol. 7, Jan. 7, pp. 82–99.*

Sefton, M.V. et al, J. Control. Release, 1992, vol. 19 (1–3), pp. 289–297.*

Roda, A et al, Analytica Chimica Acta, vol. 294(1), 1994, pp. 35–42.*

Andreopoulos, A et al, 1992, J. Appl. Polymer Sci., vol. 45(6), Jun. 25.*

* cited by examiner

ASSAY METHOD WITH IMPROVED RELEASE OF SOLUBLE REAGENTS

This is a §371 of PCT/GB95/02236, filed Sep. 20, 1995.

The present invention relates to an improved assay method and to devices for use in such methods. In particular the invention relates to assay methods, especially immunoassays, in which soluble releasable reagents are used.

The method and devices are, in certain embodiments, intended for use in specific binding assay procedures, in particular immunoassay procedures. Examples of such procedures in which soluble releasable reagents may be employed are cited in EP-A-0171148, WO92/09892, WO93/25892 and WO93/25908.

In the assay procedures disclosed in EP-A-0171148, certain ancillary reagent(s) are employed and can be in the form of a releasable reagent coating e.g. a coating of releasable antigen or antibody, or derivative thereof. In WO92/09892, in which a device is described possessing one or more calibration regions for the purposes of internal referencing of an assay method, the use of a polyvinyl alcohol (PVA) capping layer is disclosed, in order to delay the dissolution of the soluble reagent for a few seconds after the addition of the sample to the device. This delayed-release is to prevent the reagents washing from one zone to another thereby precluding an accurate assay. However, although limited effectiveness has been achieved by use of such a capping layer, problems of poor reproducibility and low sensitivity have still been encountered.

In the assay procedures disclosed in WO92/09892, the success of the method of assay depends on the spatial separation (i.e. non-mixing) of the various soluble reagents released into the sample solution. However, in other assay techniques involving only one soluble reagent it is advantageous to ensure a maximum amount of the released reagent remains in a certain defined area to ensure high assay precision and sensitivity.

Additionally, WO-A-93/025908 (ARS Holdings NV) refers generally to the delayed release properties of a coated patch and suggests PVA as a suitable material for such a patch. However, there is no suggestion that cross-linked PVA may be used as a delayed release agent.

We have now found that by employing alternative reagents for delaying the release of soluble reagents in assays unexpected improvements in the assay precision and sensitivity can be achieved as compared with the existing methods used.

Thus according to a first aspect of the present invention, we provide in assays utilising one or more soluble releasable reagents the use of cross-linked PVA or of copolymers of methacrylic acid or methacrylate esters in order to achieve the delayed-release of said soluble releasable reagents.

According to a further aspect of the present invention, we provide a method of improving assay precision in assays utilising one or more soluble releasable reagents in which the release of said reagents is delayed by means of cross-linked PVA or copolymers of methacrylic acid or methacrylate esters.

The present technique may be used for a wide variety of chemical or biochemical test procedures but is especially useful in connection with clinical test procedures, most especially immunoassays.

According to a further aspect of the present invention, there is provided a sensor device for an assay as defined above which carries on a surface thereof one or more soluble releasable reagents coated with or incorporated in cross-linked PVA or copolymers of methacrylic acid or methacrylate esters.

The present method is applicable to a wide variety of devices including, for example, dip-stick or test-strip sensors, devices using a "sample flow-through" configuration or devices employing sample containment. Sample containment devices are preferred for carrying out the method of the invention, with a more preferred device being a capillary fill device, especially a fluorescence capillary device, for example the type of device described in EP-A-171148 or in WO-90/14590. Such capillary fill devices may be used singly or in a suitable holder such as described in WO-90/1830.

As described in EP-A-171148, a capillary fill device (hereinafter CFD) typically consists of two plates of transparent material, e.g. glass, separated by a narrow gap or cavity. One plate acts as an optical waveguide and carries an immobilised reagent appropriate to the test to be carried out in the device. As described in WO-90/14590, the other transparent plate can carry on its surface remote from the cavity a layer of light-absorbing or opaque material. For use in a competition assay, the immobilised reagent may for example be a specific binding partner to the ligand desired to be detected and one of the plates may carry a dissoluble reagent comprising ligand analogue, labelled with a fluorescent dye (the ancillary reagent). When a sample is presented to one end of the CFD it is drawn into the gap by capillary action and dissolves the ancillary reagent. In a competition assay for an antigen, the fluorescently labelled antigen analogue will compete with sample antigen for the limited number of antibody binding sites immobilised onto the waveguide. Because the capillary gap is narrow (typically about 100 microns) the reaction will generally go to completion in a short time, possibly less than 5 minutes depending upon the sample matrix, assay type (e.g. sandwich or competitive immunoassay) and antibody affinity. Thus for a competition assay, the amount of fluorescently labelled antigen which becomes indirectly bound to the waveguide by virtue of complex formation will be inversely proportional to the concentration of antigen in the sample. In a sandwich assay, the waveguide will carry a specific binding partner for the ligand desired to be detected and one of the plates will carry a dissoluble reagent comprising a further specific binding partner labelled with a fluorescent dye (the ancillary reagent). In a sandwich immunoassay for an antigen, a sample antigen will form a sandwich complex with a fluorescently labelled antibody and an antibody immobilised on the waveguide. Thus, for a sandwich immunoassay, the amount of fluorescently labelled antibody which becomes indirectly bound to the waveguide by virtue of complex formation will be directly proportional to the concentration of antigen in the sample.

In the above assay techniques, it is important that the soluble releasable fluorescently labelled reagent does not dissolve instantaneously and get washed down to one end of the device away from the region of the capture antibody during filling of the CFD. If this does happen then poor assay signals are obtained with very high imprecision producing a meaningless result. The method of the present invention ensures that the wash-down of the soluble reagent is minimised.

Thus, according to a further aspect of the present invention, we provide a specifically-reactive sample-collecting and testing device possessing a cavity or cavities each having a dimension small enough to enable sample liquid to be drawn into the cavity by capillary action wherein a surface of the cavity carries an immobilised reagent appropriate to the assay to be carried out in the device, and wherein said surface is a surface of a transparent solid plate which in use acts as a light transmissive waveguide and which forms a wall of the cavity, and wherein the cavity surface(s) have one or more zones comprising, in releasable form, ancillary reagent(s) suitable for the desired assay, said ancillary reagent(s) being coated with or incorporated in cross-linked PVA or copolymers of methacrylic acid or methacrylate esters.

To provide a suitable delayed release of the soluble reagent by means of cross-linked PVA, two methods can be employed. In a first method, the soluble reagent is microdosed on the device. The reagent is dissolved in a buffer solution containing PVA. A further layer of PVA is then coated, suitably spray-coated, over the printed conjugate, this PVA layer subsequently being cross-linked, suitably by spray coating with a cross-linking reagent. In a second method, the soluble reagent is microdosed on the device. The reagent is dissolved in a buffer solution containing PVA. A cross-linking reagent is then applied, suitably by spray-coating, cross-linking the PVA present in the initial solution.

Both methods result in the production of a cross-linked film of PVA on the surface of the device (coating the soluble reagent or incorporating it). In use in assay techniques, a further coating of humectant can be applied if desired, e.g. by spray-coating a sucrose/lactose solution. This aids wetting of the device by the sample, facilitates filling of a device of the sample-containment type, and improves the stability of the reagents on storage.

The preferred reagent for cross-linking the PVA is a tetraborate solution e.g. sodium tetraborate, although other cross-linking reagents can be employed. It has been found that using about an 0.5–2% solution of tetraborate provides good results, with the best results being obtained by using about a 1% solution.

To provide a suitable delayed release of the soluble reagent by means of a copolymer of methacrylic acid or methacrylate esters, the soluble reagent is microdosed on the device. The reagent is dissolved in a buffer solution (the solution possibly also containing PVA), a film of polymer solution is then applied, preferably by spray-coating. Again, a suitable humectant coating can be applied if desired.

Suitable polymers have the required properties of swellability/porosity and preferred copolymers of methacrylic acid or methacrylate esters are those that have a time constant of swelling within the time taken for the assay to be performed and swell to give a pore size suitable to allow the soluble reagent to diffuse out. Especially useful are the reagents marketed as EUDRAGITS™ by Röhm Pharma. Eudragit NE 30 D provides especially good results. Also of use is Eudragit RL.

The polymer reagents should desirably be pH independent. Alternatively, particularly for blood or serum based assays the polymer reagents desirably swell between pH 7 and 8. For urine samples, there is often a wide variation in the pH of the samples. Use of polymers which are pH-dependent i.e. which swell at various pH levels enables one to achieve a pH cut off for assays, i.e. to select only those samples which have the desired pH range.

The method of the invention is particularly applicable to assays of antigens or antibodies, i.e. to immunoassays, and in a preferred embodiment of the invention the ligand under assay is an antigen and the specific binding partner comprises an antibody to the said antigen. However, the invention is not to be taken as limited to assays of antibodies or antigens. Examples of ligands which may be assayed by the improved assay method of the invention are given in Table 1 below, together with an indication of a suitable specific binding partner in each instance.

TABLE 1

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used in assays for: hormones, including peptide hormones (e.g. thyroid stimulating hormone (TSH), luteinizing hormone (LH), human chorionic gonadotrophin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and antibodies, alphafetoprotein (AFP) and prostate specific antigen (PSA)), drugs (e.g. digoxin, drugs of abuse), sugars, toxins, vitamins, viruses such as influenza, para-influenza, adeno-, hepatitis, respiratory and AIDS viruses, virus-like particles or microorganisms.

It will be understood that the term "antibody" used herein includes within its scope:

(a) any of the various classes or sub-classes of immunoglobulin, e.g. IgG, IgA, IgM, or IgE derived from any of the animals conventionally used, e.g. sheep, rabbits, goats or mice, (b) monoclonal antibodies, (c) intact molecules or "fragments" of antibodies, monoclonal or polyclonal, the fragments being those which contain the binding region of the antibody, i.e. fragments devoid of the Fc portion (e.g. Fab, Fab', F(ab')$_2$), the so-called "half-molecule" fragments obtained by reductive cleavage of the disulphide bonds connecting the heavy chain components in the intact antibody or fragments obtained by synthetic methods, (d) antibodies produced or modified by recombinant DNA techniques, including "humanised antibodies".

The method of preparation of fragments of antibodies is well known in the art and will not be described herein.

The term "antigen" as used herein will be understood to include both permanently antigenic species (for example, proteins, peptides, bacteria, bacterial fragments, cells, cell fragments and viruses) and haptens which may be rendered antigenic under suitable conditions.

The method of the present invention is applicable to the normal range of sample types e.g. urine, serum-based and whole-blood samples. However, particularly striking improvements over the prior art techniques are found when performing assays on whole-blood samples.

BRIEF DESCRIPTION OF THE DRAWINGS

For a better understanding of the present invention, reference is made to the accompanying drawings wherein.

DESCRIPTION OF THE INVENTION

Figure 3:
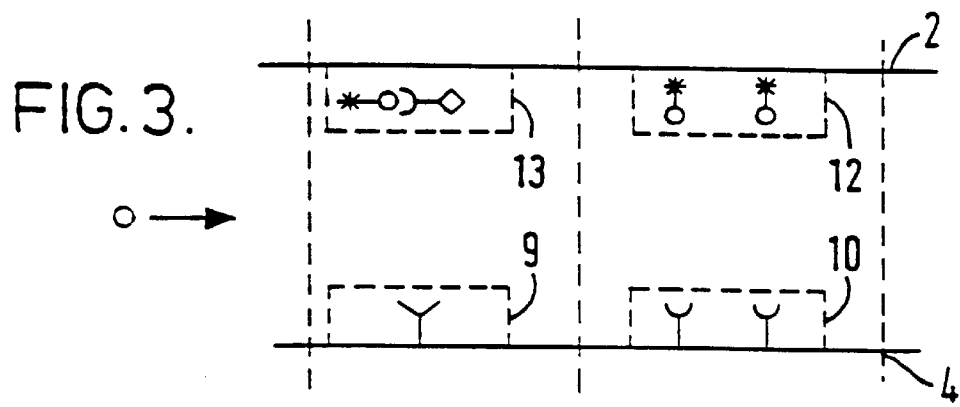
FIG. 3 illustrates schematically an example of the regions of an FCFD possessing a calibration region according to one embodiment of the present invention.
Figure 4:
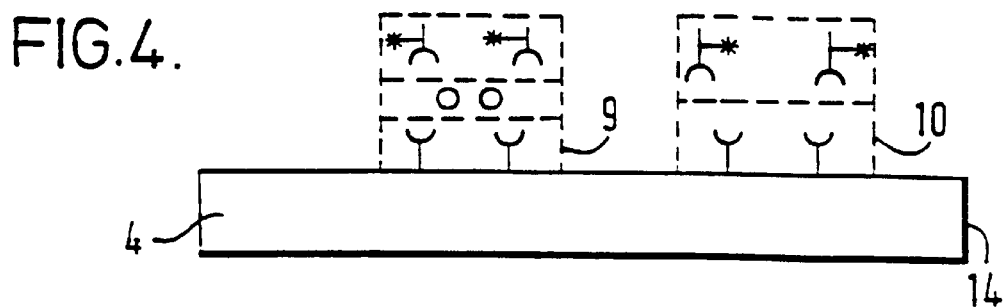
FIG. 4 shows a diagrammatic section through a dip-stick type device additionally illustrating schematically an example of the regions of such a device possessing a calibration region according to one embodiment of the present invention.

In FIGS. 3 and 4, the symbols illustrated denote the following entities:

| | |
|---|---|
| ○ | Antigen under assay |
| —* | fluorescent label |
| ○—* | fluorescently labelled antigen analogue |
| —⊂ or ◇—⊂ | specific antibody to antigen under assay |
| —⊰ | specific antibody to specific antibody to antigen under assay. |

Figure 1:
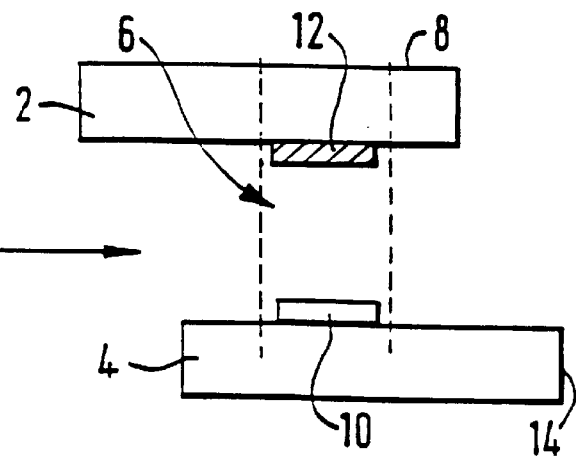
FIG. 1 shows a diagrammatic section through a fluorescence capillary device (hereinafter FCFD) according to one embodiment of the present invention.

Referring to FIG. 1, the device depicted comprises an upper plate 2 fashioned of transparent material (e.g. of plastic material, quartz, silica or glass) carrying on its external face an opaque coating 8, and a lower plate 4 fashioned of transparent material, both plates being around 1 mm thick and fixed together in substantially parallel relationship, less than 1 mm apart by means of bonding tracks of suitable adhesive containing spacer means (not shown). In the embodiment shown, the cell cavity 6 so formed is open to the surroundings at both ends, so that when liquid sample is drawn into one opening of the cavity by means of capillarity, air may escape through the other opening. In the embodiment shown, the two plates are offset.

Carried on the inner surface of the upper plate 2 is a patch of reagent 12 appropriate to the test being carried out. The reagent is contained within the device in a soluble releasable form but such release is delayed according to the method of the present invention.

Carried on the inner surface of the lower plate 4 is a patch of reagent 10 appropriate to the test being carried out, said patch 10 being directly below patch 12 on the plate 2. In the case of an immunoassay, the patch 10 will carry, for example, an amount of relevant immobilised antibody or antigen or hapten.

The operation in use of an embodiment of the device shown in FIG. 1 will now be described. Although the following description relates to the use of a device in a labelled-antigen format competition-type immunoassay, it should be understood that devices according to the invention are also suitable for use in labelled-antibody format immunoassays (both competition-type and sandwich-type) and in other types of assay (sandwich-type or competition-type) or in other types of chemical or biochemical tests.

The sample liquid passes into the device in the direction of the arrow shown in FIG. 1. A short time after the cavity 6 fills with sample liquid, the patch 12 of material dissolves, releasing the reagents contained therein into the liquid.

As mentioned hereinbefore, the patch 12 is carried on the upper plate 2 by means of suitable soluble material(s). Suitable soluble materials include humectant coatings, e.g. sucrose- or sorbitol-based. The reagent in patch 12 is coated with or is incorporated in cross-linked PVA or copolymers of methacrylic acid or methacrylate esters to provide delayed release of the reagent within the patch. A suitable coating according to the present invention would take typically 2–10 seconds to dissolve after initial contact with a sample liquid.

In one embodiment of the device of the type shown in FIG. 1 which is set up for a competition-type immunoassay for an antigen, patch 12 may contain a fluorescently labelled antigen analogue. Patch 10 would then comprise an amount of immobilised specific binding partner being a specific antibody to the antigen under assay. Thus, after introduction of the sample liquid, the patch 12 dissolves, releasing antigen analogue into the sample liquid. Antigen introduced in the sample liquid competes with antigen analogue for epitopic binding sites on the specific antibody to the antigen contained in patch 10. The amount of fluorescent material which becomes bound to the immobilised specific antibody in patch 10 will therefore be a function of the concentration of antigen in the sample liquid. Conventional competition-type optical immunoassays involve this type of competitive equilibrium.

The delayed-release of the reagent in patch 12 ensures that a maximum amount of fluorescent material remains in the region bounded by patches 10 and 12 after the device has filled and this minimising of the washdown of the reagent provides an increase in assay precision and sensitivity.

Figure 2:
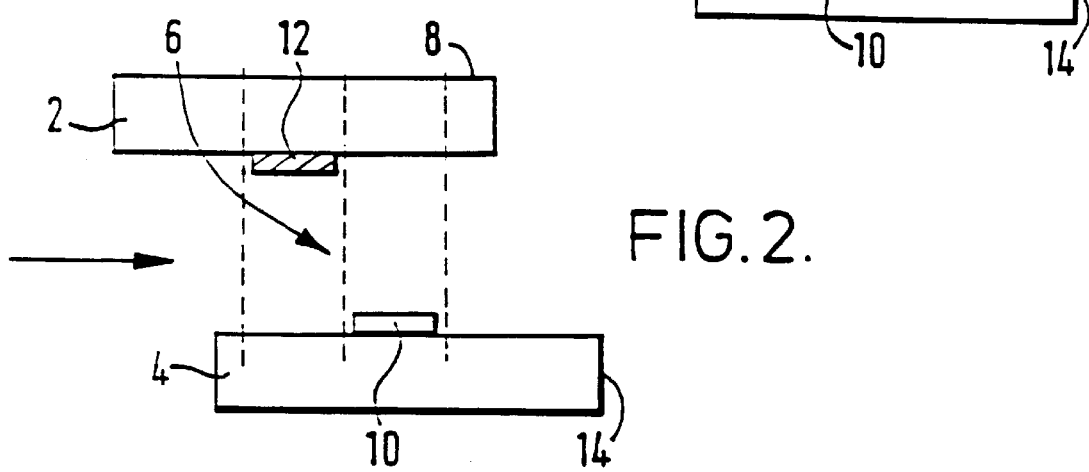
FIG. 2 shows a diagrammatic section through an FCFD used to illustrate the method of the present invention.

Referring to FIG. 2, the device depicted is not one which would be used in an assay method but is designed to demonstrate the effectiveness of the present invention. The device is essentially the same as that illustrated in FIG. 1, except patch 12 is offset as compared to patch 10. Thus, in use in an assay procedure, on filling the device with sample and performing the assay the amount of fluorescently labelled reagent which becomes bound in patch 10 will be a measure of the washdown of reagent from patch 12. By comparing existing assays, including those utilising known delayed-release techniques, with those according to the present invention the improvement provided by the present invention can be demonstrated.

In FIG. 3, the device depicted comprises an upper plate 2, and a lower plate 4 as in the device of FIG. 1. Carried on the inner surface of plate 2 is a patch 12 and carried on the inner surface of plate 4 is a patch 10, these patches and the reagents contained therein being as described above in respect of FIG. 1. Patches 9 and 13 carried on plates 2 and 4 as shown comprise a calibration region. The release of the reagents in patches 12 and 13 in use is delayed according to the method of the present invention. In use, in the region bounded by the pair of patches 9 and 13 an initial high signal will arise from the region 9 due to binding of the complex from patch 13 to the immobilised reagent in patch 9. This signal will decrease over time as ligand competes with the labelled ligand analogue in the complex in patch 9. The delayed release of the reagents from patches 12 and 13 ensures that a maximum amount of the respective reagents is released into the regions bounded by the pair of patches 10 and 12 and 9 and 13. A minimum of washdown of the reagent from patch 13 to the adjacent region occurs. These factors maximise the precision and sensitivity of the assay.

In FIG. 4, the device depicted comprises only a lower plate 4, as in the device in FIG. 1. Carried on the surface of plate 4 is a zone 10 containing a patch of reagents appropriate to the test being carried out. In the case of an immunoassay, the zone will carry, for example an amount of unlabelled relevant immobilised antibody directed to a first epitope of the ligand under assay and an amount of a labelled antibody directed to a second epitope of the ligand under assay, the labelled antibody being present in soluble releasable form, but the release of the reagents in use being delayed according to the method of the present invention. Also carried on the surface of plate 4 is a calibration zone 9 containing a patch of reagents appropriate to the test being carried out. In the case of an immunoassay, the zone will carry, for example, an amount of unlabelled relevant immobilised antibody directed to a first epitope of the ligand under assay, an amount of a labelled antibody directed to a second epitope of the ligand under assay and an amount of the antigen under assay such that a 1:1:1 complex between the antigen and the two antibodies forms under the operation of the assay, the labelled antibody and the antigen under assay being present in soluble releasable form, but the release of the reagents in use being delayed according to the method of the present invention.

The operation in use of an embodiment of the device shown in FIG. 4 will now be described. Although the examples of reagents and the following description relates to the use of a device in a labelled antibody format sandwich-type immunoassay, it should be understood that the devices are also suitable in labelled antigen format immunoassays and in other types of assay (competition-type) or in other types of chemical or biochemical tests.

The device is dipped into the sample liquid and a short time thereafter the soluble reagents in patches 9 and 10 dissolve. The delayed release of these reagents according to the present invention ensures that the reagents remain substantially within the regions shown. Thus region 10 provides the assay measurement and region 9 provides a calibration region with an initial high signal. The limited transfer of soluble reagents between the regions maximises the precision and sensitivity of the assay.

The following Examples serve to illustrate the applicability of the method of the present invention without, however, limiting it.

COMPARATIVE EXAMPLE 1

Preparation of Starting Materials 1.1 Fabrication of antibody-coated optical waveguides:

Anti-PSA monoclonal antibodies were supplied by Serono Diagnostics S A, Coinsins, Switzerland. A sheet of Permabloc glass (Pilkington Glass Ltd., St. Helens, UK) having a thickness of about 1 mm was cleaned with detergent (e.g. Tween 20) in ultra-pure water with ultrasonic agitation. The surface of the glass was activated by incubating it in a 2% solution of aminopropyltrimethoxysilane in water (pH 3–4) for two hours at 75° C. After rinsing in water the glass sheet was dried at 115° C. for at least four hours. The glass was then incubated for 60 minutes in a 2.5%. solution of glutaraldehyde in a 0.05 M phosphate buffer (pH 7) and then washed thoroughly with distilled water. Anti-PSA antibody was patterned onto the glass by discretely dosing a 1% solution of the antibody in phosphate buffer (pH 7) onto the glass and incubating it for 2 to 4 hours (to form patch 10) after which the glass sheet was washed with buffer solution. Unwanted adsorbed protein was removed by soaking with 6 M urea solution in a known manner. Finally a layer of sucrose/lactose was formed over the surface of the glass sheet by spin coating. This formed plate 4 of the FCFD test device as illustrated in FIG. 1.

1.2. Preparation of anti-PSA antibody conjugated to allophycocyanin (APC):

A second anti-PSA monoclonal antibody, which recognises a different epitope on the PSA molecule to the antibody used in 1.1 above, was conjugated to allophycocyanin ($\lambda$ex=650 nm, $\lambda$em=660 nm) by Molecular Probes Inc., Eugene, Oreg., USA and was used as supplied.

1.3. Microdosing of the specific reagents over a discrete zone of anti-PSA antibody:

An opaque coating was screen printed onto a clean sheet of Permabloc glass as described in PCT/GB90/00764. The measurement zone of the device was fabricated by microdosing a layer of allophycocyanin/anti-PSA antibody conjugate in buffer containing Polyvinyl alcohol in an area 3×7 mm onto the glass over the zone. After the conjugate was air dried a layer of polyvinyl alcohol (4% in buffer) was microdosed over the conjugate (to form patch 12). Finally the whole sheet of glass was coated in a layer of sucrose/lactose by spray coating. This formed plate 2 of the FCFD test device as illustrated in FIG. 1.

1.4. Fabrication of FCFD test devices:

FCFD test devices such as have been described in EP-A-0171148 were fabricated by screen printing onto the waveguide resulting from 1.1 above bonding tracks of an ultraviolet curing glue (UVS 91, Norland Inc., USA) containing glass microspheres of 100 $\mu$m diameter (Jencons Ltd., UK) in a pattern defining the long edges of the capillary cell devices. A sheet of glass as defined in 1.3 above was then placed over the waveguide and a vacuum applied to the laminate. As a result of the vacuum the upper sheet of glass was caused to press down onto the glue, the glass microspheres defining a gap of 100 $\mu$m between the glass sheets. The laminate was then exposed to an ultraviolet light source to cure the glue. Finally, the laminate sheet was broken into individual test devices as described in EP-A-0171148.

1.5. Apparatus used in the measurement of the PSA assay:

A simple fluorimetry apparatus as described in WO92/09892 was used to make suitable assay measurements as described in PCT/GB90/00764.

Assay Procedure for PSA:

Samples of heparinised whole blood containing known amounts of PSA were added to the FCFD device and incubated at room temperature for 20 minutes. Six FCFDs were used to produce a "reduced" standard curve (i.e. 0, 10 and 100 ng/mL PSA) with pairs of devices being filled with the same PSA concentration. The data presented in Table 1 shows that a poor standard curve results, there being a low top signal and poor replication between pairs of FCFD devices. This is caused by the whole blood sample entering the device and "instantly" dissolving the allophycocyanin/ anti-PSA antibody conjugate and transporting down the length of the FCFD away from the region in which the capture antibody is located.

COMPARATIVE EXAMPLE 2

FCFD Whole Blood Assay for PSA without using any Delayed Release Chemistry and Having no Microdosed Assay Reagents 2.1. Fabrication of antibody-coated optical waveguides:
As for Example 1.
2.2. Preparation of anti-PSA antibody conjugated to allophycocyanin (APC):

As for Example 1.
2.3. Fabrication of FCFD test devices:
   As for Example 1.
2.4. Apparatus used in the measurement of the PSA assay:
   As for Example 1.
Assay Procedure for PSA:
   Equal volumes of the allophycocyanin/anti-PSA antibody conjugate were mixed with whole blood samples containing PSA and added to the FCFD. The assays were read in the same way as in Example 1. The data show (Table 2) that there is a good dose/response curve for the FCFD whole blood assay.

EXAMPLE 3

3.1. Fabrication of antibody-coated optical waveguides:
   As for Example 1.
3.2. Preparation of anti-PSA conjugated to allophycocyanin (APC):
   As for Example 1.
3.3. Microdosing of the specific reagents over a discrete zone of anti-PSA antibody:
   As for Example 1 except that, after the antibody was microdosed, Eudragit NE 30D (Röhm Pharma, Germany) was spray-coated on top of the conjugate.
3.4. Fabrication of FCFD test devices:
   As for Example 1.
3.5. Apparatus used in the measurement of PSA assay:
   As for Example 1.
Assay Procedure for PSA:
   As for Example 1 except that, due to the presence of the Eudragit, the dissolution of the antibody/fluorophore conjugate was delayed until the sample had filled the FCFD. This resulted in the PSA assay showing better precision between replicates and giving a higher top signal (Table 3).

EXAMPLE 4

4.1. Fabrication of antibody-coated optical waveguides:
   As for Example 1.
4.2. Preparation of anti-PSA conjugated to allophycocyanin (APC):
   As for Example 1.
4.3. Microdosing of the specific reagents over a discrete zone of anti-PSA antibody:
   As for Example 1 except that, after the antibody was microdosed, a 0.24% solution of tetraborate in water was spray-coated on top of the conjugate to cross link the polyvinyl alcohol present in the microdosing solution.
4.4. Fabrication of FCFD test devices:
   As for Example 1.
4.5. Apparatus used in the measurement of the PSA assay:
   As for Example 1.
Assay Procedure for PSA:
   As for Example 1 except that, due to the presence of the cross-linked polyvinyl alcohol, the dissolution of the antibody/fluorophore conjugate was delayed until the sample had filled the FCFD. This resulted in the PSA assay showing better precision between replicates and giving a higher top signal (Table 4).

EXAMPLE 5

Optimisation of Tetraborate Concentration 5.1. Fabrication of antibody-coated optical waveguides:
   As for Example 1.
5.2. Preparation of anti-PSA antibody conjugated to allophycocyanin (APC):

As for Example 1.
5.3. Microdosing of the specific reagents over a discrete zone of anti-PSA antibody:
   As for Example 1 except that, after the antibody was microdosed, solutions of a range of tetraborate concentrations in water were spray-coated on top of the conjugate to cross-link the polyvinyl alcohol present in the microdosing solution.
5.4. Fabrication of FCFD test devices:
   As for Example 1.
5.5. Apparatus used in the measurement of the PSA assay:
   As for Example 1.
Assay Procedure for PSA:
   As for Example 1 except that, due to the presence of the cross-linked polyvinyl alcohol, the dissolution of the antibody/fluorophore conjugate was delayed until the sample had filled the FCFD. The optimum delayed release was given by 1% tetraborate (Table 5).
   Although the figures in Table 5 suggest that using 0.5% tetraborate gives a higher top signal/background signal ratio, repeating the assay did not give such good reproducability as was found when using 1% tetraborate. Hence using 1% tetraborate gave better assay precision.

EXAMPLE 6

FCFD Whole Blood Assay for PSA Using Known and Present Delayed Release Methods 6.1. Fabrication of antibody coated optical waveguides:
   As for Example 1 except that the capture antibody was immobilised over a region to form patch 10 of a device as illustrated in FIG. 2.
6.2. Preparation of anti-PSA antibody conjugated to allophycocyanin (APC):
   As for Example 1.
6.3. Microdosing of the specific reagents over a discrete zone of anti-PSA antibody:
   As for Example 1 except that the specific reagents were microdosed in a region to form patch 12 of a device as illustrated in FIG. 2. After microdosing of the reagents some devices were treated with tetraborate whilst others were not.
6.3. Fabrication of FCFD test devices:
   As for Example 1.
6.4. Apparatus used in the measurement of the PSA assay:
   As for Example 1.
Assay Procedure for PSA:
   Whole blood samples containing PSA were added to the FCFD and the assay signal from region 10 was read. Where only a known PVA capping layer was present there was in effect no delayed release within the FCFD and the soluble reagents washed down the device giving a dose/response curve for the PSA assay (Table 6). When the delayed release method of the present invention was employed in the FCFD the amount of reagent washed down the device was less giving a much reduced dose/response curve (Table 6).
   The figure of 8.580 at a PSA concentration of 50 ng/ml in Table 6 shows the imprecision of the existing technique of merely including a PVA capping layer. Similarly the assay curve in such a method tends to be skewed i.e. showing a large background signal.
   It should be noted that in the Examples given above different conjugates were used in various of the Examples, the conjugates being of varying quality i.e. giving a different maximum signal. Some Examples used a conjugate with a lower colour intensity, others used a conjugate with a higher colour intensity. Thus a straight comparison of the top signals obtained in the assays should not in general be made between the Examples since this factor of varying intensity will not be taken into account in such a comparison.

TABLE 1

Known PVA capping layer present in the FCFD

| PSA Concentration (ng/mL) | Signal (Arbitrary Units) | Mean Signal (Arbitrary Units) |
|---|---|---|
| 0 | 0.465 | 0.412 |
|  | 0.384 |  |
|  | 0.386 |  |
| 10 | 1.259 | 1.174 |
|  | 1.458 |  |
|  | 0.805 |  |
| 100 | 1.430 | 1.823 |
|  | 1.432 |  |
|  | 2.607 |  |

TABLE 2

Dose/response characteristics for an FCFD assay for PSA in whole blood using pre-mixed reagents

| PSA concentration (ng/mL) | Signal (Arbitrary units) | Mean Signal (Arbitrary units) |
|---|---|---|
| 0 | 0.581 | 0.545 |
|  | 0.508 |  |
| 10 | 1.531 | 1.506 |
|  | 1.480 |  |
| 100 | 4.666 | 4.688 |
|  | 4.710 |  |

TABLE 3

Eudragit delayed release reagent present in the FCFD.

| PSA Concentration (ng/mL) | Signal (Arbitrary Units) | Mean Signal (Arbitrary Units) |
|---|---|---|
| 0 | 0.665 | 0.646 |
|  | 0.561 |  |
|  | 0.713 |  |
| 10 | 1.262 | 1.287 |
|  | 1.226 |  |
|  | 1.373 |  |
| 100 | 2.069 | 2.012 |
|  | 2.010 |  |
|  | 1.956 |  |

TABLE 4

Cross-linked polyvinyl alcohol delayed-release reagent present in the FCFD

| PSA Concentration (ng/mL) | Signal (Arbitrary Units) | Mean Signal (Arbitrary Units) |
|---|---|---|
| 0 | 0.665 | 0.646 |
|  | 0.561 |  |
|  | 0.713 |  |
| 10 | 1.262 | 1.287 |
|  | 1.226 |  |
|  | 1.373 |  |
| 100 | 2.069 | 2.012 |
|  | 2.010 |  |
|  | 1.956 |  |

TABLE 5

Effect of variations in the tetraborate concentration.

| Tetraborate concentration (%) | PSA concentration (ng/mL) | Signal (Arbitrary units) |
|---|---|---|
| 0.5 | 0 | 0.525 |
|  | 10 | 2.554 |
|  | 100 | 6.872 |
| 1.0 | 0 | 0.479 |
|  | 10 | 2.138 |
|  | 100 | 6.089 |
| 1.5 | 0 | 0.481 |
|  | 10 | 1.961 |
|  | 100 | 4.913 |
| 2.0 | 0 | 0.459 |
|  | 10 | 1.857 |
|  | 100 | 5.398 |

TABLE 6

Effect of PVA/tetraborate delayed release method.

| Treatment | PSA Concentration (ng/mL) | Signal (Arbitrary units) |
|---|---|---|
|  | 0 | 1.546 |
| known PVA capping | 5 | 2.539 |
| layer | 10 | 4.086 |
| (essentially no | 50 | 8.580 |
| delayed release | 100 | 6.195 |
| chemistry) |  |  |
|  | 0 | 0.514 |
| PVA plus | 5 | 0.850 |
| tetraborate | 10 | 1.855 |
| (present delayed | 50 | 1.980 |
| release method) | 100 | 2.390 |

What is claimed is:

1. In a method of conducting an assay for an analyte in which one or more reagents soluble in the assay medium are dissolved in the assay medium and interact in the assay medium with another entity leading to an indication of the presence or absence of the analyte and wherein said reagent is in a form in which the dissolution of said reagent into the assay medium when contacted with the assay medium is delayed, the improvement which comprises said form being an association of said reagent with a delayed release agent comprising cross-linked polyvinyl alcohol wherein individual polymer chains are linked together by covalent bonds, whereby the precision of the assay is improved.

2. A method as claimed in claim 1 wherein the assay is a whole blood sample.

3. A sensor device for use in a method as claimed in claim 1 which carries on the surface thereof one or more soluble releasable agents coated with or incorporated in a delayed release agent comprising a cross-linked polyvinyl alcohol wherein individual polymer chains are linked together by covalent bonds.

4. A sensor device as claimed in claim 3 being a sample containment device.

5. A sensor device as claimed in claim 4 being a capillary fill device.

6. A sensor device as claimed in claim 5 being a fluorescence capillary fill device.

7. A process for preparing a sensor device as claimed in claim 3, said process including the following steps:
   (a) dissolving the soluble releasable reagent in a buffer solution,
   (b) microdosing the soluble releasable reagent buffer solution on an appropriate surface of a sensor device,
   (c) providing polyvinyl alcohol by including it in the buffer solution or by coating the microdosed reagent with a layer thereof, or both, and
   (d) introducing a cross-linking agent onto the soluble releasable agent in order to cross-link the polyvinyl alcohol wherein individual polymer chains are linked together by covalent bonds, and
   (e) optionally introducing a soluble carrier material being a humectant.

8. A process as claimed in claim 7 in which cross-linking is carried out by means of a tetraborate solution.

9. A process as claimed in claim 8 in which the tetraborate solution is an approximately 1% solution.

10. A method as claimed in claim 1 in which the assay is a specific binding assay.

11. A method as claimed in claim 10 wherein said assay is an immunoassay.

12. A method as claimed in claim 10 wherein the soluble releasable agent is in admixture with the delayed release agent.

13. A method as claimed in claim 10 wherein the soluble releasable agent is coated with the delayed release agent.

* * * * *